United States Patent [19]

Ning et al.

[11] Patent Number: 4,739,049

[45] Date of Patent: Apr. 19, 1988

[54] PHOSPHORYLATION OF CYCLIC AMIDES

[75] Inventors: Robert Y. Ning, West Caldwell; Pradeep B. Madan, Lake Hiawatha, both of N.J.

[73] Assignee: Hoffmann-La Roche Inc., Nutley, N.J.

[21] Appl. No.: 897,456

[22] Filed: Aug. 15, 1986

Related U.S. Application Data

[63] Continuation of Ser. No. 715,149, Mar. 22, 1985, abandoned, which is a continuation of Ser. No. 395,931, Jul. 7, 1982, abandoned, which is a continuation of Ser. No. 966,528, Dec. 4, 1978, abandoned, which is a continuation of Ser. No. 758,728, Jan. 12, 1977, abandoned, which is a continuation of Ser. No. 574,653, May 6, 1975, abandoned.

[51] Int. Cl.$^4$ .................. C07D 243/14; C07D 487/04
[52] U.S. Cl. .......................... 540/563; 540/542; 540/566; 540/571; 540/572
[58] Field of Search ............... 540/542, 563, 566, 571, 540/572

[56] References Cited

U.S. PATENT DOCUMENTS 4,349,477 9/1982 Walser et al. .................... 260/244.4

OTHER PUBLICATIONS

Ning et al, J. Org. Chem., vol. 41, No. 16 (1976) pp. 2720–2727.

*Primary Examiner*—Richard L. Raymond
*Attorney, Agent, or Firm*—Jon S. Saxe; Bernard S. Leon; Richard J. Mazza

[57] ABSTRACT

Compounds of the general formula

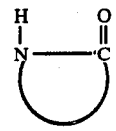

are reacted with a strong base followed by a phosphorylating agent, such as dicyclicaminophosphinic halide or bis-di-lower alkylaminophosphinic halide to produce an imine of the formula

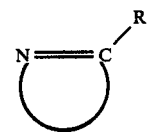

wherein R is dicyclicaminophosphinyloxy or bis-di-lower alkylaminophosphinyloxy.

R represents a leaving group which will undergo nucleophilic displacement with nitrogen, oxygen, sulfur and carbon containing nucleophiles, that is, nucleophiles which have, as a reactive site, a nitrogen, oxygen, sulfur or carbon atom, such that, when the cyclic imine undergoes nucleophilic displacement, there is formed C—N, C—O, C—S and C—C bonds between the carbon atom of the cyclic imine and the nucleophilic group.

The end products may be utilized as intermediates in the production of pharmaceutically valuable compounds and, in some instances, are pharmaceutically valuable compounds per se.

3 Claims, No Drawings

PHOSPHORYLATION OF CYCLIC AMIDES

This is a continuation of application Ser. No. 715,149 filed Mar. 22, 1985, now abandoned which is a continuation of Ser. No. 395,931, filed July 7, 1982, now abandoned which is a continuation of Ser. No. 966,528, filed Dec. 4, 1978, now abandoned, which is a continuation of Ser. No. 758,728, filed Jan. 12, 1977, now abandoned, which is a continuation of Ser. No. 574,653, filed May 6, 1975, now abandoned.

DESCRIPTION OF THE INVENTION

This invention relates to a process for preparing compounds of the formula

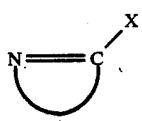

wherein X- represents a nucleophilic group of the nitrogen, oxygen, sulfur and carbon type.

Following the process of the present invention, one can prepare compounds of formula I by the reaction of cyclic amide compounds of the general formula

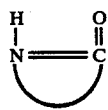

with a strong base followed by a phosphorylating agent such as dicyclicaminophosphinic halide or bis-di-lower alkylaminophosphinic halide to produce an imine of the formula

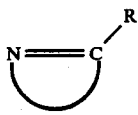

wherein R is a leaving group of the formula

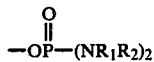

wherein $R_1$ and $R_2$ separately are lower alkyl, allyl, phenyl, and substituted phenyl groups or together with the nitrogen atom form a substituted or unsubstituted heterocyclic ring of 3–8 atoms, e.g., aziridine, azetidine, pyrrolidine, 3-pyrroline, piperidine, 4-methylpiperidine, piperazine, morpholine, hexamethyleneimine, heptamethyleneimine.

The compound of formula III may then be reacted with nucleophilic radicals represented by the symbol X- wherein X- stands for nucleophiles of the nitrogen, oxygen, sulfur and carbon type, which results in the displacement of the leaving group R and the formation of C—N, C—O, C—S and C—C bonds, i.e., compounds of the formula

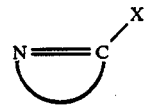

As used in this disclosure the term "lower alkyl" or "alkyl" comprehends both straight and branched chain ($C_1$–$C_7$) carbon-hydrogen radicals, preferably $C_1$–$C_4$ carbon-hydrogen radicals such as methyl, propyl, ethyl, isopropyl, butyl and the like.

By the term "dicyclicamino" is meant a 3 to 8-membered heterocyclic ring structure such as dipiperazino, dipiperidino, dipyrrolidino and dimorpholino.

By the term "cyclic amide" is meant a ring system of 4 to 10 atoms which is heterocyclic in nature; and which contains an amide group. As used in this disclosure, such a ring system may be a monocyclic ring, i.e., containing two or more rings produced by fusing other ring systems with the "cyclic amide" as, for example, a benzodiazepine.

Nucleophilic agents, i.e., compounds which displace the phosphinyl group resulting in the formation of C—N, C—O, C—S and C—C bonds, are of the nitrogen, oxygen, sulfur and carbon type. Nucleophilic agents of the nitrogen type include ammonia, primary and secondary amines, or alkali metal salts of primary and secondary amines. Examples of the above include monoalkylamines such as monomethylamine and monoethylamine, dialkylamines such as diethylamine, aromatic primary and secondary amines such as aniline and monomethyl-aniline, cyclic amines such as morpholine, piperidine, and pyrrolidine, hydrazine, 2-hydrazinopyridine and substituted hydrazines such as 1,1-dimethylhydrazine, 1,2-dimethylhydrazine, methylhydrazine, 4-nitrophenylhydrazine, phenylhydrazine and 2,2,2-trifluoroethylhydriazine, functionalized derivatives of the above amines such as 2-hydroxyethylamine (ethanolamine), 2-aminoethylamine (ethylenediamine), carbalkoxymethylamine, glycine esters, methyl hydrazinocarboxylate, acetylhydrazide, hydroxylamine, N-methylhydroxylamine, and N-ethylhydroxylamine; alkoxylamines such as methoxylamine, ethoxylamine; acyl and aroylhydrazides such as acetylhydrazide, methylhydrazinocarbozylate, butyl carbazate, carbohydrazine, p-aminobenzoyl hydrazide, and cyanoacetohydrazide. Also included are other amino and hydrazino gropus containing multi-functional molecules such as N-acetyl-L-tyrosine hydrazide and the like. Also included as nucleophiles of the nitrogen type are anionic nitrogen species derived from the treatment of oximes, amides, ureas and imines with suitably strong bases such as alkali metal hydrides (e.g., n-butyl lithium), for example, the anions derived from acetone oxime, acetamide, N,N-dimethylurea, 2-iminopropane.

Nucleophilic agents of the sulfur type include thiols (mercaptans) such as allyl mercaptan, N-acetylcysteine, benzyl mercaptan, cyclohexyl mercaptan, furfuryl mercaptan, thiolactic acid, mercaptosuccinnic acid and the like or mercapto groups containing compounds in combination with a tertiaryamine such as pyridine or triethylamine as proton acceptors. The thiols may be hydrogen sulfide, aliphatic thiols such as methyl or ethyl mercaptan, aryl thiols such as thiophenol and heteroaromatic thiols such as mercaptopyridine.

Also included as suitable nucleophiles of the sulfur type are the anions derived from the treatment of thioamides and thioureas with a suitably strong base such as alkali metal hydrides (e.g., sodium hydride), for example, the anions derived from thiourea, N,N-dimethylthiourea, thioformamide, thioacetamide, N-methylthioacetamide and the like.

Nucleophiles of the carbon type refers to a well known class of anionic carbon species commonly called carbanions, or in combination with the counter metallic cations as salts or organometallic reagents. Carbanions are commonly generated from the corresponding hydrogen-bearing carbon species with suitably strong bases (e.g., $\underset{\sim}{1} \rightarrow \underset{\sim}{2}$)

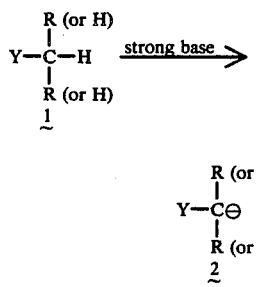

such as methyl lithium, sodium hydride, potassium tertiarybutoxide and methyl magnesium chloride. Alternately, the corresponding halogen bearing compounds 3 may be treated with certain zero-valent metals such as lithium, magnesium and zinc (e.g., $\underset{\sim}{3} \rightarrow \underset{\sim}{2}$) to give the same anions $\underset{\sim}{2}$. In the context of this invention, we limit the definition of the metal counter cation of $\underset{\sim}{2}$ to that of potassium, sodium, lithium and magnesium. The reactivities of these cabanions are known to be modified by the substituents attached to the carbon bearing the negative charge. For the purpose of this invention, carbanions of suitable reactivities must be chosen; the choice is based on firstly, that the carbanion has sufficient reactivity toward displacing the R leaving group in the particular molecule of structural type II, and secondly, that the carbanions should not be so reactive that it would not be compatible with compounds of type II and the intended products III.

The most suitable carbanions for our purpose are those represented by $\underset{\sim}{2}$ in which Y stands for one of the groups listed below (a-q) and the remaining two substituents are independently hydrogen or lower alkyl. Also listed are one example in each category of $\underset{\sim}{2}$ of the corresponding compound $\underset{\sim}{1}$ from which these anions can be derived:

(a) alkoxycarbonyl or aryloxycarbonyl

e.g., ethyl acetate
(b) acyl or aroyl

e.g., acetone
(c) dialkylaminocarbonyl

(d) cyano (N≡C—), e.g., acetonitrile
(e) nitro (O$_2$N—), e.g., nitromethane
(f) N-alkyl-N-nitrosoamino

e.g., N-nitrosodiethylamine
(g) pyridinium

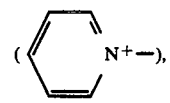

e.g., 1-methylpyridinium iodide
(h) triphenylphosphonium ((C$_6$H$_5$)$_3$P±), e.g., methyl triphenylphosphonium bromide
(i) dialkylphosphonyl or diarylphosphonyl

e.g., dimethyl methylphosphonate
(j) alkylsulfonyl or arylsulfonyl

e.g., dimethylsulfone
(k) alkylsulfinyl or arylsulfinyl

e.g., dimethylsulfoxide
(l) dialkylsulfonium (R$_2$S⊕—) e.g., trimethylsulfonium iodide
(m) dialkylsulfoxonium

e.g., trimethylsulfoxonium iodide
(n) N,N-dialkylsulfamoyl or N,N-diarylsulfamoyl

e.g., N,N-dimethylmethanesulfonamide
(o) N,N-dialkylaminosulfinyl

e.g., N,N-dimethylmethanesulfonamide
(p) dihydro-1,3-oxazin-2-yl

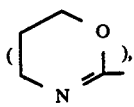

e.g., 4,5-dihydro-2-methyl-6H-1,3-oxazine
(q) phenyl and substituted phenyl

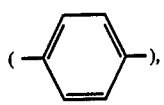

e.g., 4-nitrotoluene

Also suitable for the purpose of this invention are carbanions in which the carbon bearing the negative charge is attached to two stabilizing groups, the third group being hydrogen or lower alkyl, i.e., formula $\underline{4}$.

Here Y and Y' are independently one of the following groups: alkyloxy, aryloxy, alkylthio, arylthio and substituents a, b, c, d, f and q as defined above for the monosubstituted carbanions. Alternatively, Y and Y' together may form a heterocyclic ring system of 5 to 8 atoms. Examples of carbanions of type $\underline{4}$ are the well known anions derived from malonic acid diesters such as dimethylmalonate, acetoacetic acid esters such as ethyl acetoacetate, 1,3-pentanedione, malononitrile, N,N,N',N'-tetramethylmalonamide, 1-cyanoacetylpiperidine, ethyl 2-cyanoacetate and methyl 2-phenylacetate.

Certain carbanions with three stabilizing substituents are also suitable for the purpose of this invention. An example of this group are the anions of dimethyl 2-acetamidomalonate and the corresponding diethyl ester.

In addition to the carbanions described above, the anions of alkenes (olefins, i.e., $\underline{5}$) and alkynes (acetylenes, i.e., $\underline{6}$) also fall within the scope of this invention.

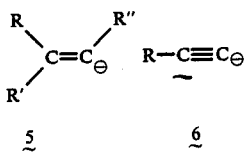

Examples of reagents of this type are vinyl magnesium chloride, lithium phenylacetylide, vinyl lithium and propynyl lithium.

Nucleophilic agents of the oxygen type include alkali metal salts of alcohols such as sodium methoxide and sodium ethoxide. Alternatively, free alcohols such as methanol and propanol and diols such as ethylene glycol and propylene glycol may be used together with a tertiary amine, as proton acceptor, such as pyridine and triethylamine.

By the term "lower alkanoyl" as utilized herein, an acyl moiety of a $C_1$-$C_7$ preferably a $C_1$-$C_4$ alkanoic acid is intended, e.g., acetyl, propionyl, butyryl and the like, i.e., moieties of the formula

wherein R is $C_1$-$C_3$ or hydrogen.

By the terms "halogen, halide or halo" is meant all four halogens, i.e., iodine, fluorine, bromine and chlorine with the latter two preferred.

By the term "alkali metal" is meant monovalent elements such as lithium, sodium, potassium and the like.

By the term "alkoxy carbonyl" is meant compounds such as methoxycarbonyl, ethoxycarbonyl and the like.

In a preferred aspect of the present invention the starting material of formula II is a 1,4-benzodiazepin-2-one of the general formula

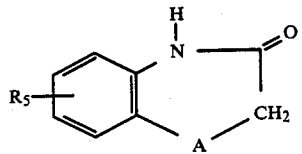

wherein A is selected from the group consisting of

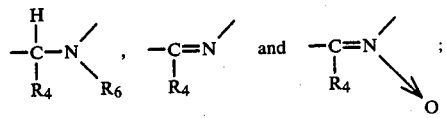

$R_5$ is selected from the group consisting of hydrogen, halogen, nitro, cyano, trifluoromethyl, lower alkyl, amino, hydroxy lower alkyl and lower alkanoyl; $R_4$ is selected from the group consisting of phenyl, mono-substituted phenyl, di-substituted phenyl, pyridyl, mono-substituted pyridyl, thiophenyl, pyrimidinyl, oxazolyl, thiazolyl groups and 1-cyclohexenyl groups; $R_6$ is selected from the group consisting of hydrogen, lower alkyl, acyl, and lower alkoxycarbonyl so that by following the novel process of the present invention there is obtained sa compound of the formula

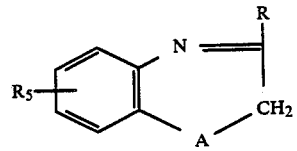

wherein R, $R_5$, A, $R_4$ and $R_6$ are as above.

The compounds of formula IIIA may then be reacted with well known nucleophiles which will displace the R leaving group while not attacking other reactive sites on the molecule to produce compounds of the formula

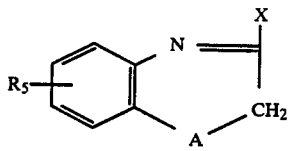 IA wherein $R_5$, A and X- are as above.

The compounds of formula IIA and formula IA wherein a starting material of the formula IIA type is employed are per se active as sedatives, anticonvulsants and muscle relaxants. Further, compounds (IA) may be reacted to produce other compounds having sedative, anticonvulsant and muscle relaxant activities, for example, imidazo [1,5-a][1,4]benzodiazepine compounds which may be produced utilizing compounds of the formula IA. Such a further process and utilization of compounds of formula IA is set forth in copending U.S. patent application Ser. No. 504,924 filed Sept. 11, 1974 continued respectively in Ser. No. 602,691, filed Aug. 7, 1975, abandoned, Ser. No. 633,660, filed Mar. 4, 1976, abandoned, Ser. No. 904,951, filed May 11, 1978, abandoned, and Ser. No. 178,208, filed Aug. 14, 1980, now U.S. Pat. No. 4,307,237.

Yet another series of compounds which may be produced by utilizing compounds of formula IA are the triazolobenzodiazepines which are known compounds of pharmaceutical value. The present process is particularly useful in this instance since the end products of this process need not be isolated, that is, the triazolobenzodiazepines can be formed in situ without the isolation of formula IA compounds of the present process and thereafter subsequent reaction. A preferred aspect of this process is set forth below.

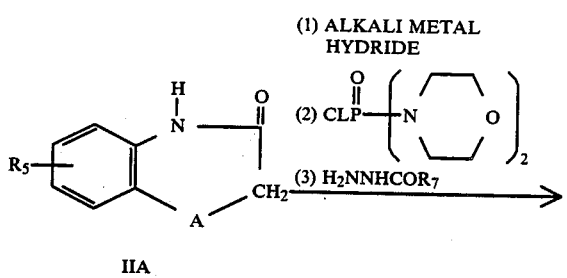

IIA

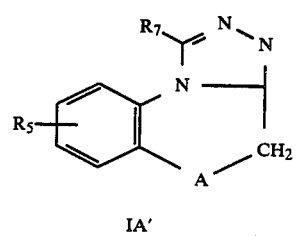

IA' wherein $R_5$, A, $R_4$ and $R_6$ are as above and $R_7$ is selected from the group consisting of hydrogen, lower alkyl, COO lower alkyl, a radical of the formula

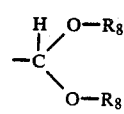

wherein $R_8$ is lower alkyl and a radical of the formula

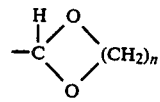

wherein n is 2 to 5.

Although a dimorpholinophosphinic chloride is shown as utilized in the above reaction, any suitable dicyclicaminophosphinic halide or bis-di-lower alkylaminophosphinic halide may be utilized to achieve the above reaction. Similarly, instead of the alkali metal hydride, there may be utilized alkali metal alkoxides such as potassium tertiary butoxide or sodium methoxide and alkyl lithium compounds such as n-butyl lithium.

Most preferred of the compounds of formula IA are those wherein $R_5$ is halogen e.g., chlorine, and is on the 7-position of the molecule and wherein A is

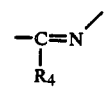

with $R_4$ preferably being monosubstituted phenyl most preferably ortho-substituted i.e., a compound of the formula:

7-chloro-1,3-dihydro-2-nitromethylene-5-(2-fluorophenyl)-2H-1,4-benzodiazepine.

Most preferred of the compounds of formula IA' are those wherein $R_5$ is 8-position and is halogen, e.g., chlorine, wherein A is

with $R_4$ preferably being monosubstituted phenyl, most preferably being ortho-substituted, i.e., in the 2'-position of the phenyl, with a halogen e.g., fluoro or chloro and $R_7$ is hydrogen or lower alkyl i.e., a compound of the formula:

8-chloro-6-(2-chlorophenyl)-1-methyl-4H-s-triazolo[4,3-a][1,4]benzodiazepine.

Representative of benzodiazepin-2-ones which may be utilized as starting materials (formula IIA compounds) are the following known compounds which are commercially available or can be prepared in analogy to the preparation of known compounds, e.g., 7-bromo-1,3-dihydro-5-phenyl-2H-1,4-benzodiazepin-2-one;

7-chloro-5-(2-chlorophenyl)-1,3-dihydro-2H-1,4-benzodiazepin-2-one;

1,3-dihydro-7-nitro-5-phenyl-2H-1,4-benzodiazepin-2-one;

7-chloro-1,3-dihydro-5-phenyl-2H-1,4-benzodiazepin-2-one;

7-nitro-5-(2-chlorophenyl)-1,3-dihydro-2H-1,4-benzodiazepin-2-one;

7-bromo-5-(2-pyridyl)-1,3-dihydro-2H-1,4-benzodiazepin-2-one.

In another preferred aspect of the present invention, the starting material consists of a 1,4-benzodiazepin-5-one of the general formula

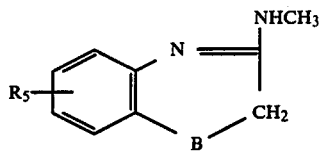

wherein B is

and R₅ is as above so that by following the novel process of the present invention there is obtained a compound of the formula

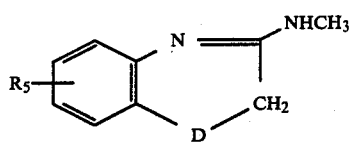

wherein D is

and R and R are as above.

The compound of formula IIIB may then be reacted with nucleophiles as defined above which will displace the R leaving group to produce compounds of the formula

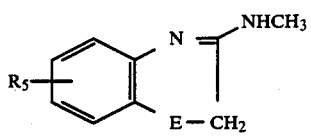        IB wherein R₅ and X⁻ are as above the E is

Compounds of formula IB are per se active as sedatives, muscle relaxants and anticonvulsants, see, for example, U.S. Pat. No. 3,678,038.

Compounds of formula IB may be utilized as intermediates to produce various known 5-substituted benzodiazepine compounds, for example, compounds of the formula

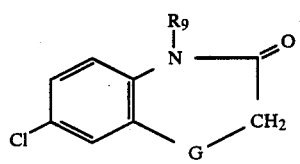        IB' wherein G is

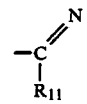

,

R₉ is hydrogen or lower alkyl, R₁₁ is NH(CH₂)ₙN(CH₃)₂ or OR₉ and n is 0 to 4.

The compounds of formula IB' exhibit stimulant and antidepressant activity, see, for example, French Pat. No. 5,614 issued Jan. 15, 1968.

1,4-Benzodiazepin-5-ones which may be utilized as starting materials (formula IIB compounds) are known compounds which are commercially available or can be prepared in analogy to the preparation of known compounds, see, for example, U.S. Pat. No. 3,678,038.

In another preferred aspect of the present invention, the starting material consists of a carbostyril of the formula

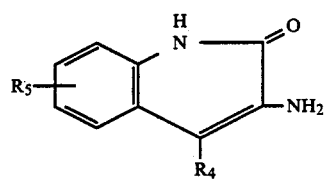        IIC wherein R₅ and R₄ are as above, so that by following the novel process of the present invention there is obtained a compound of the formula

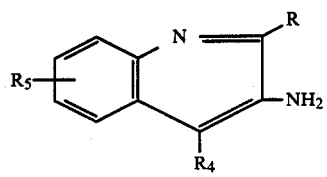        IIIC wherein R, R₄ and R₅ are as above.

Compounds of formula IIIC are then reacted with nucleophiles as defined above which will displace the R leaving group to produce compounds of the formula

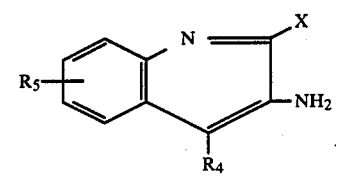        IC wherein R₅, R₄ and X⁻ are as above.

Compounds of formula IC wherein a starting material of the formula IIC type is utilized may be further reacted to produce indoloquinolines, compounds which are useful as antitumor agents, i.e., they inhibit the growth of transplantable tumors. Such a further process and utilization of the above end products (formula I compounds) to produce indoloquinolines is set forth in copending U.S. Application Ser. No. 395,871 filed Sept. 10, 1973 continued in Ser. No. 596,684, filed July 16, 1975, now U.S. Pat. No. 4,014,883.

The starting materials of the formula IIC type are known compounds. Examples of such compounds are found in an article entitled "Synthetic Methods for the Preparation of 3-Amino-2[IH]-quinolones", by Fryer et al., Journal of the Chemical Society (London), pages 3097–3101, 1964.

Most preferred of the compounds of formula IB are those wherein $R_5$ is halogen, e.g., chlorine, and is on the 7-position of the molecule and wherein E is

with X being methylamino, i.e., a compound of the formula:

7-chloro-2,5-bismethylamino-3H-1,4-benzodiazepine

Most preferred of the compounds of formula IC are those wherein $R_5$ is halogen, e.g., chlorine and is on the 7-position of the molecule, wherein $R_4$ is phenyl and wherein X is methylthio, i.e., a compound of the formula:

3-amino-6-chloro-2-methylthio-4-phenyl-quinoline.

In another preferred aspect of the present invention the starting material consists of a 3-benzazepin-2-one of the formula

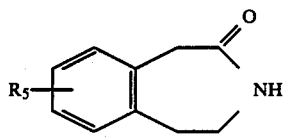 IID wherein $R_5$ is as above so that by following the novel process of the present invention there is obtained a compound of the formula

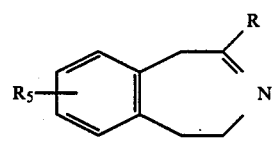 IIID wherein R and $R_5$ are as above.

The compund of formula IIID may then be reacted with nucleophiles as defined above which will produce a compound of the formula

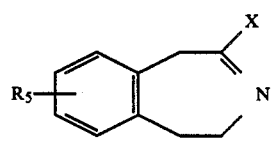 ID wherein $R_5$ is X- are as above.

The final compounds of the formula D are useful as intermediates in the production of benzazepine derivatives which exhibit analgesic activity, e.g., benzazepine derivatives disclosed in U.S. Pat. No. 3,719,669 issued Mar. 6, 1973 and J. Hetero. Chem. 2, 26–36, 1965.

The starting materials utilized are known materials; see, for example, I. L. Knunyants and B. P. Fabrichnyi, Doklady Alad. Nauk SSSR 68, 523 (1949); Chem. Abstr. 44, 1469 (1950).

In another preferred aspect of the present invention the starting materials of formulas IIE and IIE' consist of compounds of the formulas

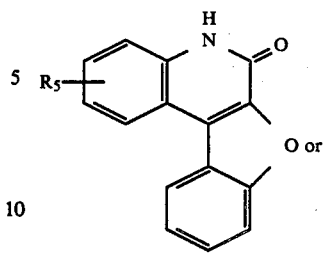 IIE

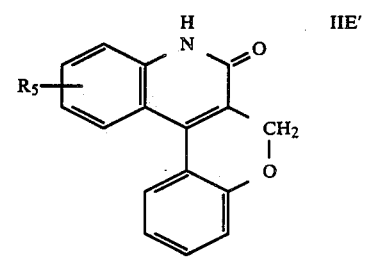 IIE' wherein $R_5$ is as above so that by following the novel process of the present invention there are obtained compounds of the formulas

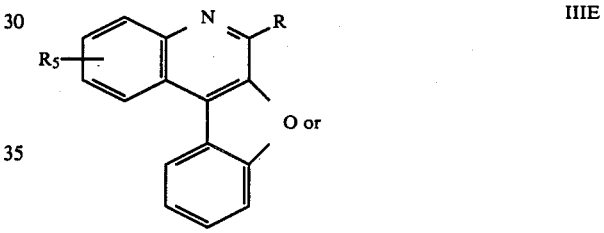 IIIE

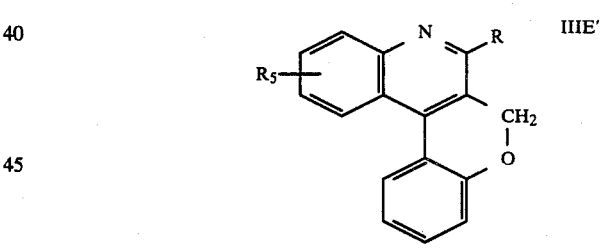 IIIE' wherein $R_5$ and R are as above.

The compounds of formula IIIE and IIIE' may then be reacted with well known nucleophiles, as above, which will displace the R leaving group while not attacking other reactive sites on the molecule to produce compounds of the formula

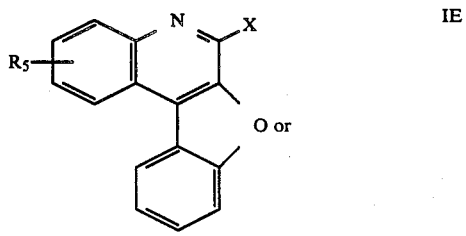 IE

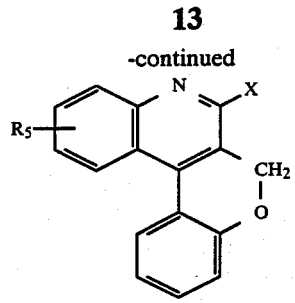

wherein $R_5$ and X- are as above.

The compounds of formulas IE and IE' exhibit activity and are useful as antitumor agents, i.e., they inhibit growth of transplantable tumors.

The reaction of the compounds of formula II (A–E') with a phosphorylating agent to yield the corresponding compounds of formula III (A–E') accomplished after treatment of compounds of formula II with a strong base sufficient to ionize the formula II compound to form the corresponding anion. Suitable bases include alkali meta alkoxides such as potassium tertiary butoxide or sodium methoxide and alkali metal hydrides such as sodium hydride and alkyl lithium compounds such as n-butyl lithium. The reaction may be effected at temperatures of about 0° C. to about 100° C. but preferably at about room temperature. The reaction is conveniently carried out in an aprotic polar ineert solvent, i.e., one that would solubilize the ambient salts of the formula II compounds totally or at least partially. Preferred solvents include ethers such as tetrahydrofuran and dioxane and tertiary amides such as dimethylformamide (DMF). In the most preferred embodiment of the above reaction the starting material is initially treated with one molar equivalent of strong base.

The nucleophilic displacement reactions of the compounds of formula III with various nucelophilic agents is preferably carried out at temperatures of about −80° C. to about 100° C. Most preferred is room temperature. As above, an aprotic polar inert solvent may be utilized to solubilize the reaction compounds. Suitable solvents include ethers such as tetrahydrofuran or dioxane and tertiary amides such as dimethylformamide.

The compounds of formula II above used as the starting materials for this process are known or can be prepared in analogy to the preparation of known compounds.

The following examples are illustrative of the scope of the present invention. The temperatures are given in degrees Centigrade unless otherwise indicated.

EXAMPLE 1

7-Chloro-2-di-(moropholino)phosphinyloxy-5-phenyl-3H-1,4-benzodiazepine

To a solution of 5.4 g. (20 mmoles) of 7-chloro-1,3-dihydro-5-phenyl-2H-1,4-benzodiazepin-2-one in 100 ml. of dry tetrahydrofuran at room temperature was added 1.2 g. of a 50% dispersion of sodium hydride in oil (25 mmoles of hydride). The mixture was warmed gently on the steambath, under nitrogen, for approximately 1 hour until hydrogen evolution stopped. To this mixture was added 7.5 g. (30 mmoles) of dimorpholinophosphinic chloride. The resulting mixture was stirred at room temperature for 2 hours. Insoluble salts were removed by filtration and the solvent was evaporated. The residue crystallized from ethyl acetate to give the desired product, m.p. 189°–191°. An analysis sample was prepared by recrystallization from methylene chloride-ether-petroleum ether to give colorless prisms, m.p. 184°–186° d.

EXAMPLE 2

7-Chloro-2-methylamino-5-phenyl-3H-1,4-benzodiazepine (a) From 7-chloro-2-di-(morpholino)phosphinyl-5-phenyl-3H-1,4-benzodiazepine To a solution of 487 mg. (1.0 mmole) of 7-chloro-2-di-(morpholino)phosphinyloxy-5-phenyl-3H-1,4-benzodiazepine in 10 ml. of tetrahydrofuran at room temperature was introduced a stream of methylamine gas for 10 minutes. Solids precipitated during the addition. The solvent was evaporated and the residue was partitioned between methylene chloride and water. The methylene chloride layer was dried and evaporated. Crystallization of the residue from methylene chloride-hexane yielded, in two crops, the product having a m.p. of 245°–247°.

(b) From 7-chloro-1,3-dihydro-5-phenyl-3H-1,4-benzodiazepine-2-one

To a solution of 271 mg. (1 mmole) of 7-chloro-1,3-dihydro-5-phenyl-3H-1,4-benzodiazepin-2-one in 10 ml. of dry tetrahydrofuran at room temperature was added 57.6 mg. of a 50% dispersion of sodium hydride in oil (1.2 mmoles of hydride). The mixture was warmed gently on the steam bath for approximately 1 hour until hydrogen evolution stopped. To this mixture was added 382 mg. (1.5 mmoles) of dimorpholinophosphinic chloride. The resulting mixture was stirred at room temperature for 2 hours. To this mixture was introduced a stream of methylamine gas (in excess) for 20 minutes. Tetrahydrofuran was evaporated and the residue was partitioned between methylene chloride and water. The methylene chloride layer was dried and evaporated. Crystallization from methylene chloride-hexane yielded the final product.

EXAMPLE 3

7-Chloro-1,3-dihydro-5-phenyl-2H-1,4-benzodiazepin-2-thione

To a stirred solution of 245 mg. (0.5 mmole) of 7-chloro-2-di-(morpholino)phosphinyloxy-5-phenyl-3H-1,4-benzodiazepine in 10 ml. of tetrahydrofuran containing 0.5 ml. of triethylimine at room temperature was introduced a stream of hydrogen sulfide gas until tlc indicated that all the starting material was consumed (15 minutes). Tetrahydrofuran was evaporated. The residue was partitioned between methylene chloride and water. The methylene chloride layer was dried and evaporated. Crystallization of the residue from methanol yielded, in two crops, a product having a melting point of 243°–245°.

EXAMPLE 4

7-Chloro-2-methoxy-5-phenyl-3H-1,4-benzodiazepine

To a solution of 24.5 mg. (0.5 mmoles) of 7-chloro-2-di-(morpholino)phosphinyloxy-5-phenyl-3H-1,4-benzodiazepine in 5 ml. of methanol at room temperature was added 82 mg. (1.5 mmoles) of sodium methoxide. The mixture was left at room temperature overnight. Methanol was evaporated and the residue was slurried with ether. Insoluble salts were removed by filtration. The clear ether solution was evaporated. Crystallization of the residue from petroleum ether yielded a final product having a m.p. of 94°–97°.

EXAMPLE 5

7-Chloro-1,3-dihydro-2-nitromethylene-5-phenyl-2H-1,4-benzodiazepine

To a mixture of 1.0 ml. of nitromethane and 5 ml. of dry dimethylformamide was added 53 mg. of a 50% dispersion of sodium hydride in mineral oil (1.1 mmole hydride). After 1 hour at room temperature, under nitrogen, 489 mg. (1.0 mmole) of 7-chloro-2-di-(morpholino)phosphinyloxy-5-phenyl-3H-1,4-benzodiazepine was added. After stirring at room temperature for 2 hours, dimethylformamide was evaporated (about 80°). The residue was partitioned between methylene chloride and an aqueous layer which is acidified with a slight excess of acetic acid. The methylene chloride layer was dried ($Na_2SO_4$) and evaporated. Separation of the product mixture by preparative tlc (silica gel, developed in 10% methanol in ethylacetate v/v) afforded pure final product, which upon crystallization from methanol, had a m.p. of 178°–180°.

EXAMPLE 6

7-chloro-1,3-dihydro-2-(dimethoxymalonylidene)-5-phenyl-2H-1,4-benzodiazepine

To a solution of 489 mg. (1.0 mmole) of 7-chloro-2-di-(morpholino)phosphinyloxy-5-phenyl-3H-1,4-benzodiazepine in 5 ml. of dry dimethylformamide at room temperature was added 130 mg. (1.15 mmoles) of potassium tert-butyl alcoholate and 0.5 ml. of dimethyl malonate. The resulting dark mixture was kept at room temperature for 2 hours, then warmed on the steam bath for 0.5 hour. The solvent was evaporated and the desired product was isolated by using preparative thin layer chromatography. Crystallization from isopropanol yielded a product having a m.p. of 130°–133°.

EXAMPLE 7

8-Chloro-1-methyl-6-phenyl-4H-s-triazolo[4,3-a][1,4]benzodiazepine (a) From 7-chloro-2-di-(morpholino)phosphinyl-5-phenyl-3H-1,4-benzodiazepine To a solution of 74 mg. (1 mmole) of acethydrazide in 5 ml. of butanol was added 245 mg. (0.5 mmole) of 7-chloro-2-di-(morpholino)phosphinyloxy-5-phenyl-3H-1,4-benzodiazepine. The mixture was heated to reflux for 1 hour. The solvent was evaporated and the residue was partitioned between methylene chloride and water. The methylene chloride layer was washed with water, dried and evaporated. The residue was crystallized from methylene chloride-ether to give, in two crops, a final product having a m.p. of 226°–228°.

(b) From 7-chloro-1,3-dihydro-5-phenyl-2H-1,4-benzodiazepin-2-one

To a solution of 1.08 g. (4 mmoles) of 7-chloro-1,3-dihydro-5-phenyl-2H-1,4-benzodiazepin-2-one in 20 ml. of dry tetrahydrofuran at room temperature was added 230 mg. of a 50% dispersion of sodium hydride in oil (4.8 mmoles of hydride). The mixture was warmed gently on the steam bath approximately 1 hour until hydrogen evolution stopped. Dimorpholinophosphinic chloride (1.53 g., 6 mmoles) was added and the resulting mixture was stirred at room temperature for 2 hours. To this mixture was then added to a solution of 593 mg. (8 mmoles) of acethydrazide in 5 ml. of butanol and stirring was continued at room temperature for 10 minutes. Solvents were evaporated and the residue was dissolved in 10 ml. of butanol and heated to reflux for 1 hour. Butanol was evaporated and the residue was partitioned between methylene chloride and water. The methylene chloride layer was dried and evaporated. The residue was crystallized from methylene chloride-ether to give a final product having a m.p. of 223°–225°.

EXAMPLE 8

8-Chloro-6-(2-chlorophenyl)-1-methyl-4H-s-triazolo[4,3-a][1,4]-benzodiazepine

To a solution of 610 mg. (2 mmoles) of 7-chloro-5-(2-chlorophenyl)-1,3-dihydro-2H-1,4-benzodiazepin-2-one in 10 ml. of dry tetrahydrofuran at room temperature was added 115 mg. of a 50% dispersion of sodium hydride in oil (2.4 mmoles of hydride). The mixture was warmed gently on the steam bath for approximately 1 hour until hydrogen evolution stopped. Dimorpholinophosphinic chloride (764 mg., 3.0 mmoles) was added and the resulting mixture was stirred at room temperature for 2 hours. To this mixture was then added a solution of 296 mg. (4 mmoles) of acethydrazide in 5 ml. of dry tetrahydrofuran and stirring was continued for 15 minutes at room temperature. Solvents were evaporated and the residue was dissolved in 20 ml. of butanol and heated to reflux for 2 hours. Butanol was evaporated. The residue was partitioned between methylene chloride and water. The methylene chloride layer was dried and evaporated. Crystallization of the residue from isopropanol-ether-petroleum ether yielded, in two crops, final product having a m.p. of 225°–227°.

EXAMPLE 9

8-Ethyl-6-(2-fluorophenyl)-1-methyl-4H-s-triazolo[4,3-a][1,4]-benzodiazepine 5-oxide A mixture of 1.00 g. (3.36 mmoles) of 1,3-dihydro-7-ethyl-5-(2-fluorophenyl)-2H-1,4-benzodiazepin-2-one 4-oxide, 194 mg. of a 50% dispersion in oil of sodium hydride (4.0 mmoles) and 20 ml. of dry tetrahydrofuran was stirred at room temperature for 0.5 hour. To this mixture was added 1.8 g. (7.0 mmole) of dimorpholinophosphinic chloride and the mixture was stirred at room temperature for 2 hours.

To this reaction mixture was then added a solution of 520 mg. (7.0 mmoles) of acethydrazide dissolved by warming in 5 ml. of tetrahydrofuran, and the mixture was stirred for 20 minutes. The mixture was then evaporated to dryness in vacuo, and 20 ml. of n-butanol was added. The mixture was heated to reflux for 2 hours. On cooling the mixture was evaporated to dryness in vacuo. The residual deep brownish oil was separated by preparative thin layer chromatography on twenty 20 cm.×20 cm×1.5 mm silica gel plates. The plates were developed in a 50% (v/v) mixture of ethanol and ethyl acetate. The band corresponding to the desired product was scraped off and eluted with a 50% (v/v) mixture of ethanol and ethyl acetate. The solvents were removed in vacuo and the residue on crystallization from a mixture of methylene chloride and hexane yielded the final product as straw prisms having a m.p. of 114°–117°.

EXAMPLE 10

7-Chloro-1,3-dihydro-5-(2-fluorophenyl)-2-nitromethylene-2H-1,4-benzodiazepine To a solution of 577 mg. (2 mmoles) of 7-chloro-1,3-dihydro-5-(2-fluorophenyl)-2H-1,4-benzodiazepin-2-one in 10 ml of dry tetrahydrofuran at room temperature was added 96 mg of a 50% dispersion in oil of sodium hydride (2 mmoles of hydride). The resulting mixture was stirred at room temperature approximately 1 hr until $H_2$ evolution stopped. Then 610 mg (2.4 mmoles) of dimropholinophosphinic chloride was added. The mixture was stirred at room temperature for 2 hrs, then used without isolation* in the following procedure.

*The intermediate 7-chloro-2-(bis-morpholino)phosphinyloxy-5-(2-fluorophenyl)-3H-1,4-benzodiazepine, mp 143° may be isolated at this point.

To a stirred mixture of 1.5 ml of nitromethane in 5 ml of dimethyl sulfoxide under nitrogen, and cooled in an ice bath (5°) was added in portions 220 mg (9.6 mmoles) of lithium amide. After stirring for 10 min the tetrahydrofuran suspension from above was added slowly, keeping the temperature 5°-10°. The resulting mixture was stirred at room temperature overnight. The reaction mixture was poured into ice cold aqueous acetic acid (20 mmoles) precipitating solids which were collected, washed with water and air dried. These solids (1 g) were dissolved in tetrahydrofuran and separated by column chromatography (100 g silica gel, packed in ether). The desired product was eluted with ether (275 ml) as a first yellow component. The dried residue on crystallization from ether-hexane, yielded in two crops, the desired product, identified by a comparative tlc and a mixture mp. with an authentic sample (mp 173°-175°).

EXAMPLE 11

5-(2-Chlorophenyl)-2-[bis(morpholino)phosphinyloxy]-7-nitro-3H-1,4-benzodiazepine To a stirred solution of 4.74 g (15 mmoles) of 5-(2-chlorophenyl)-1,3-dihydro-7-nitro-2H-1,4-benzodiazepin-2-one in 80 ml of dry tetrahydrofuran at room temperature was added 875 mg of a 50% dispersion of sodium hydride in oil (18 mmoles of hydride). The mixtute was stirred at room temperature for 1 hr until hydrogen evolution stopped. Dimorpholinophosphinic chloride (7.5 g, 30 mmoles) was added and the resulting mixture was stirred at room temperature for 3 hrs. Solids (mixture of product and salt) were collected and partitioned between water and methylene chloride. The methylene chloride layer was dried and evaporated. Crystallization of the residue from methylene chloride ether gave colorless needles, mp 214°-216°.

EXAMPLE 12

7-Chloro-5-(2-chlorophenyl)-2-[bis-(morpholino)-phosphinyloxy]-3H-1,4-benzodiazepine To a stirred solution of 915 mg (3.0 mmoles) of 7-chloro-5-(2-chlorophenyl)-1,3-dihydro-2H-1,4-benzodiazepin-2-one in 10 ml of dry tetrahydrofuran was added 173 mg of a 50% dispersion as sodium hydride in oil (3.6 mmoles of hydride). The mixture was stirred at room temperature approximately 1 hr until hydrogen evolution stopped. Dimorpholinophosphinic chloride (1.5 g; 6.0 mmoles) was added and the resulting mixture was stirred at room temperature for 2 hrs. Insoluble salts were removed by filtration. Tetrahydrofuran was evaporated. The residue was crystallized from ethyl acetate to give colorless needles, mp 185°-187°.

EXAMPLE 13

7-Chloro-2-(2-hydroxyethoxy)-5-phenyl-3H-1,4-benzodiazepine

A suspension of 1.95 g (4.0 mmoles) of 7-chloro-2-di-(morpholino)phosphinyloxy-5-phenyl-3H-1,4-benzodiazepin in 10 ml of ethylene glycol containing 4 ml of triethylamine was heated on a steam bath for 2 hrs. A clear solution formed soon after heating began. Triethylamine was removed in vacuo. The ethylene glycol solution was poured into ice water precipitating solids which were collected and washed thoroughly with water. Remaining water was removed from the solid by dissolving in solid in ether, drying over sodium sulfate and evaporation of ether. Crystallization of the residue from ether-hexane gave colorless prisms, mp 142°-144°.

EXAMPLE 14

7-Chloro-2-(2-methoxycarbonyl)hydrazino-5-phenyl-3H-1,4-benzodiazepine

To a stirred solution of 9.8 g (20 mmoles) of 7-chloro-2-di-(morpholino)phosphinyloxy-5-phenyl-3H-1,4-benzodiazepine in 200 ml of tetrahydrofuran at room temperature was added 3.6 g (40 mmoles) of methyl hydrazinocarboxylate. The resulting orange solution was stirred at room temperature for 2 hrs. Tetrahydrofuran was evaporated. The residue was partitioned between water and methylene chloride. Methylene chloride layer was dried and evaporated. Crystallization of the residue from ethyl acetate gave the desired product, mp 198°-200° d. An analysis sample was prepared by recrystallization from ethyl acetate to give colorless needles, mp 201°-203° d.

EXAMPLE 15

7-Chloro-5-(dimorpholino)phosphinyloxy-2-methylamino-3H-1,4-benzodiazepine

A mixture of 22 g (0.10 mole) of 7-chloro-3,4-dihydro-2-methylamino-5H-1,4-benzodiazepin-5-one 7.2 g of a 50% dispersion of sodium hydride in mineral oil (0.15 mole of hydride) and 1.5 l. of tetrahydrofuran (dried over alumina) was stirred at room temperature for 0.5 hr until hydrogen evolution ceased. To this mixture was added 51.3 g (0.20 mole) of dimorpholinophosphinic chloride and the mixture was stirred at room temperature for 2 hrs. The insolubles were removed by filtration and the filtrate was evaporated to dryness. The residue was crystallized from ethyl acetate to yield colorless prisms, mp 195°-6°.

An analytical sample was prepared by recrytallizations from ethyl acetate to yield colorless prisms, mp 210°-12°.

EXAMPLE 16

7-Chloro-2,5-bismethylamino-3H-1,4-benzodiazepine

A solution of 1.00 g (2.2 mmoles) of 7-chloro-5-dimorpholinophosphinyloxy-2-methylamino-3H-1,4-benzodiazepine in 30 ml of a 3.8M solution of methylamine in tetrahydrofuran was heated in a stoppered glass pressure bottle on a steam bath for 24 hrs. The solution was concentrated to a gum. The gum was dissolved in a small volume of ethanol. Addition of ethanolic hydrogen chloride followed by ether afforded the hydrochloride salt, mp 276°-278°.

The salt was dissolved in water, and basified with aqueous ammonia to liberate the free base. The base was isolated by entraction with methylene chloride. Crystallization from methylene chloride afforded colorless prisms mp 235°–237°. Recrystallization from ethanol raised the mp to 248°–250°.

EXAMPLE 17

7-Chloro-1,2,3,4-tetrahydro-5H-1,4-benzodiazepin-2,5-dithione

To a stirred suspension of 442 mg (1.0 mmole) of 7-chloro-5-(dimorpholino)phosphinyloxy-2-methylamino-3H-1,4-benzodiazepine in 50 ml of dry tetrahydrofuran at room temperature was introduced a stream of bubbles of hydrogen sulfide gas for 1 hr. Solids gradually dissolved and solution turned yellow. Tetrahydrofuran was evaporated. The residue was stirred with 50 ml of water and 50 ml of methylene chloride. Solids to give the desired product mp 273°–4° d. An analysis sample was prepared by recrystallization from methanol to give yellow needles, mp 273° d.

EXAMPLE 18

3-Amino-6-chloro-2-dimorpholinophosphinyloxy-4-phenyl-quinoline

To a solution of 2.7 g (10 mmoles) of 3-amino-6-chloro-4-phenylcarbostyril in 40 ml of dry (molecular seives) dimethylformamide, was added 720 mg of a 50% dispersion of sodium hydride in mineral oil (15 mmoles of hydride) and this mixture was stirred at room temperature for 0.5 hr. To this mixture was added 5.13 g (20 mmoles) of dimorpholinophosphinic chloride and the mixture was stirred at room temperature for 2 hrs. The insolubles were removed by filtration. The filtrate was evaporated to dryness in vacuo. The residue on trituration with diethyl ether gave a light brown amorphous solid mp 185°–87°.

An analytical sample was prepared by recrystallization from ethyl acetate to yield buff prisms, mp 188°–90°.

EXAMPLE 19

3-Amino-6-chloro-2-methylthio-4-phenyl-quinoline

To a stirred solution of 488.9 mg (1.0 mmole) of 3-amino-6-chloro-2-(dimorpholino)phosphinyloxy-4-phenylquinoline in 30 ml of dry tetrahydrofuran was added 4 ml of a 1M solution of sodium salt of methyl mercaptan in cellusolve. The reaction mixture was heated to reflux for 2 hrs. The resulting suspension was then allowed to cool to room temperature at which time the insoluble salts were removed by filtration. The filtrate was concentrated to an oily gum. The gum was separated by preparative thin-layer chromatography (six 20 cm×20 cm×1.5 mm silica gel plates developed in a 1:9 (v/v) mixture of ether and benzene. The desired product was isolated and crystallized from ether-hexane. The product consisted of light yellow prisms were collected, mp 115°–117°. This material was found to be identical to that of an authentic sample (mp 115°–117°) by tlc and mixture mp.

EXAMPLE 20

Bis-(Dimethylamino)phosphinic Chloride

A solution of 360 g (8.0 moles) of anhydrous dimethylamine in 1200 ml of anhydrous ether was chilled in a dry-ice acetone bath. To this solution was added over a 1 hr period a solution of 307 g (2.0 moles) of phosphoryl chloride in 122 ml of anhydrous ether. On completion of the addition, the dry-ice bath was removed and the mixture was stirred at room temperature for 3 hrs. The hydrochloride salt was removed by filtration and the ethereal filtrate was evaporated to an oil. Fractional distillation of the oil at 3 mm Hg, afforded at the boiling range of 90°–92°, 257 g (75%) of the product as a colorless oil, $N_D^{24} 1.4645$.

EXAMPLE 21

7-Chloro-1,3-dihydro-2-methylamino-5-phenyl-3H-1,4-benzodiazepine via phsophorylation of corresponding lactam with bis-dimethylaminophosphinic chloride A mixture of 540 mg (2.0 mmoles) of 7-chloro-1,3-dihydro-5-phenyl-2H-1,4-benzodiazepin-2-one, 120 mg of a 50% dispersion of sodium hydride in mineral oil (2.5 mmoles of hydride), and 10 ml of alumina dried tetrahydrofuran was stirred at room temperature for 0.5 hr, until hydrogen evolution ceased. Bis-dimethylaminophosphinic chloride (340 mg; 2.0 mmoles) was added in one portion, and the mixture was stirred at room temperature for 1 hr. A 2.8 molar solution of methylamine in tetrahydrofuran (10 ml) was added and stirring continued for 0.5 hr. The mixture was partitioned between methylene chloride and water. The methylene chloride layer was dried ($Na_2SO_4$) and evaporated to dryness. The residual oil was separated by preparative thin-layer chromatography on six 20 cm×20 cm×1.5 mm silica gel plates, developed in ethyl acetate. Some unchanged starting lactam (mp 212–215; Rf 0.61) was recovered. The product, occurring at Rf 0.39, was isolated. On crystallization from ether the product had a melting point of 240°–242°. This was found to be identical to an authentic sample of the title compound by tlc and mixture mp.

EXAMPLE 22

8-Chloro-1-methyl-6-phenyl-[4,3-a]-5-triazolo-1,4-benzodiazepine via phosphorylation of with bis-dimethylamino-phosphinic chloride:

A mixture of 540 mg (2.0 mmoles) of 7-chloro-1,3-dihydro-5-phenyl-3H-1,4-benzodiazepin-2-one, 120 mg (2.5 mmole) of a 50% dispersion of sodium hydride in mineral oil, (2.5 mmoles of hydride) and 10 ml of tetrahydrofuran (dried over alumina) was stirred for 0.5 hr until hydrogen evolution ceased. To this mixture was added 680 mg (4.0 mmoles) of bis-dimethylamino-phosphinic chloride and stirring was continued for 2 hrs. To the mixture was added 296 mg (4.0 mmoles) of acethydrazide in 10 ml of warm tetrahydrofuran, and the mixture was then evaporated to dryness in vacuo. The residue was dissolved in 20 ml of n-butanol and the solution was heated to reflux for 2 hrs. On cooling butanol was evaporated. The residue was partitioned between methylene chloride and saturated aqueous sodium bicarbonate. The organic layer was dried over anhydrous sodium sulfate, and then evaporated to dryness. The residue on crystallization from methylene chloride-ether afforded buff prisms, identical to authentic sample by tlc and mixture mp.

EXAMPLE 23

7-Chloro-2-di-(morpholino)-phosphinyloxy-5-(2-fluorophenyl)-3-methyl-3H-1,4-benzodiazepine To a stirred solution of 6 g. (0.02 m) of 7-chloro-1,3-dihydro-5-(2-fluorophenyl)-3-methyl-2H-1,4-benzodiazepin-2-one in 100 ml of dry tetrahydrofuran was added 1.05 g, (0.25 m) of 57% sodium hydride dispersion in mineral oil. The mixture was placed under argon and refluxed for 1 hr. After cooling to room temperature, the mixture was treated with 7.4 g (0.03 m) of dimorpholinophosphinic chloride and stirring under argon was continued at room temperature for 2 hrs. The mixture was filtered and evaporated at reduced pressure to give a gummy residue. Stirrring the gum with 100 ml of anhydrous ether gave white crystals which were collected by filtration, washed with a little ether and air dried. The final product has a m.p. of 90°–95°.

EXAMPLE 24

7-Chloro-1,3-dihydro-5-(2-fluorophenyl)-3-methyl-2-nitro methylene-2H-1,4-benzodiazepine A stirred solution of 2.4 g (0.04 m) of nitromethane in 50 ml of dry dimethylformamide was treated with 1 g (0.024 m) of 57% sodium hydride dispersion in mineral oil at room temperature under argon. After stirring for 1 hr. at room temperature, the mixture was treated with 5.2 g (0.01 m) of 7-chloro-2-di(-morpholino)-phosphinyloxy-5-(2-fluorophenyl)-3-methyl-3H-1,4-benzodiazepine in one portion and stirring under argon was continued at room temperature for 24 hrs. The dark mixture was poured over a mixture of ice and glacial acetic acid with stirring to give a yellow solid. Stirring was continued until the ice had melted. The solid was filtered, washed with water and air dried on the funnel to yield a product having mp of 215° dec. Recrystallization of a sample from 1:1 methanolmethylene chloride solution gave yellow needles, mp 219°–221° dec.

EXAMPLE 25

8-Chloro-1,4-dimethyl-6-(2-fluorophenyl)-4H-imidazo[1,5-a][1,4]benzodiazepine

A solution of 5.2 g (0.015 m) of 7-chloro-1,3-dihydro-5-(2-fluorophenyl)-3-methyl-2-nitromethylene-2H-1,4-benzodiazepine in 450 ml of 2:1 tetrahydrofuran-methanol was hydrogenated for 3 hrs. using a Parr apparatus, Raney nickel catalyst (3 teaspoonsful) and an initial pressure of 18 psi. The mixture was filtered and evaporated at reduced pressure to give crude 2-aminomethyl-7-chloro-2,3-dihydro-5-(2-fluorophenyl)-3-methyl-1H-1,4-benzodiazepine as a yellow oil.

The crude aminomethyl compound was mixed with 5 ml of triethyl orthoacetate, and 0.5 g of p-toluenesulfonic acid monohydrate in 100 ml of ethanol. After heating under reflux for 2 hrs, the solution was evaporated at reduced pressure. The residue was cooled to room temperature, treated with a mixture of ice and concentrated ammonium hydroxide and extracted with methylenechloride. Evaporation of the dried extracts in vacuo gave crude 8-chloro-3a,4-dihydro-1,4-dimethyl-6-(2-fluorophenyl)-3H-imidazo[1,5-a][1,4]benzodiazepine as a gum.

The crude dihydroimidazobenzodiazepine was mixed with 20 g of activated manganese dioxide and 200 ml of toluene and heated under reflux for 2 hrs. The mixture was filtered and the manganese dioxide was washed with methylene chloride. Evaporation of the combined filtrate and washings at reduced pressure gave a brown gum. The dihydrochloride of the product was obtained as a white powder by stirring the gum with ethanolic hydrogen chloride for a few minutes. The salt melted at 247°–250°.

EXAMPLE 26

7-(1-Methyl-1,3-dioxalan-2-yl)-2[bis(morpholino)phosphinyloxy]5-phenyl-3H-1,4-benzodiazepine A solution of 19.3 g. (0.06 m) of 1,3-dihydro-7-(1-methyl-1,3-dioxalan-2-yl)-5-phenyl-2H-1,4-benzodiazepin-2-one in 300 ml. of dry tetrahydrofuran was treated under an atmosphere of argon with 3.1 g. (0.075 m) of a 57% suspension of sodium hydride in mineral oil. The mixture was heated under reflux for 1 hr., cooled to room temperature when 22.2 g. (0.087 m) of dimorpholinophosphinio chloride was added. The mixture was allowed to stir at room temperature for 2 hr. and then stand overnight. Sodium chloride was removed by filtration and the crude product was obtained by removal of the solvent and crystallization of the residue from ether.

EXAMPLE 27

2,3-Dihydro-7-(1-methyl-1,3-dioxolan-2-yl)-2-nitromethylene-5-phenyl-1H-1,4-benzodiazepine A mixture of 100 ml. of dry N,N-dimethylformamide and 6.8 g. of nitromethane was treated under an atmosphere of argon with 2.8 g. (0.066 m) of a 57% suspension of sodium hydride in mineral oil. The mixture was stirred for 1 hr. at room temperature when a solution of 18 g. (0.033 m) of crude 7-(1-methyl-1,3-dioxalan-2-yl)-2[bis(morpholino)phosphinyloxy]5-phenyl-3H-1,4-benzodiazepine in 50 ml. of dry N,N-dimethylformamide was added. The reaction mixture was allowed to stand at room temperature for 15 hrs. when the dark viscous liquid was poured over a mixture of ice and dilute acetic acid. The bright yellow precipitate was removed by filtration, dissolved in dichloromethane which was washed with dilute ammonium hydroxide and water, dried over anhydrous sodium sulfate and evaporated. The original filtrate was extracted with dichloromethane which was washed, dried and evaporated as above. The two crude residues were combined and chromatographed over Florisil. Using dichloromethane, 10% (v/v) ether as the eluent and monitoring the fractions by tlc, several fractions containing the product were collected and evaporated. Crystallization and recrystallization from a mixture of dichloromethane and hexane gave the pure product as pale yellow prisms, m.p. 158°–161°.

EXAMPLE 28

2-Chlorobenzofurano[2,3-c]quinolin-6(5H)-one

Sodium hydride suspension 2.4 g (50% in mineral oil) was washed with hexane and added to a solution of 5.8 g of 6-chloro-1,2-dihydro-4-(2-fluorophenyl)-3-hydroxy-2-oxoquinoline * in 60 ml of dimethylformamide. The mixture was stirred and refluxed for 5 hrs. in an atmosphere of nitrogen. The product was precipitated by addition of water to the cooled reaction mixture. The crystals were collected, washed with water, methanol and ether to leave final product with mp>360°. The analytical sample was recrystallized from dimethylformamide.

EXAMPLE 29

2-chloro-7H-chromeno[3,4-c]quinolin-6(5H)-one

A solution of 3.5 g (0.01 mol) of ethyl 6-chloro-4-(2-fluorophenyl)quinolin-2(1H)-one-3-carboxylate,* in 50 ml of tetrahydrofuran was added to a suspension of 1 g (0.022 mol) of lithium aluminum hydride in 50 ml of tetrahydrofuran. After stirring for 30 min at −20° to 0°, the hydride was hydrolized by addition of 5 ml of water. The mixture was then partitioned between methylene chloride and 2N hydrochloric acid. The methylene chloride layer was washed with water dried and evaporated. Crystallization of the residue from ethanol/chloroform yielded 6-chloro-4-(2-fluorophenyl)-3-hydroxymethylquinolin-2(1H)-one, with mp 282°–286°.
*A Walser, A. Szente and J. Hellerbach, J. Org. Chem. 38, 449 (1973).

Sodium hydride suspension (50% in mineral oil), 10 g, was washed with hexane and added to a solution of 20 g (0.066 mol) of the 6-chloro-4-(2-fluorophenyl)-3-hydroxymethylquinolin-2(1H)one in 350 ml of dimethylformamide. This mixture was stirred and refluxed under an atmosphere of nitrogen for 5 min. The cool reaction mixture was diluted with water and the product was precipitated by acidifying with 1N hydrochloric acid. It was collected, washed with water and recrystallized from dimethylformamide to yield final product with mp>350°.

We claim:

1. A process to prepare a compound of the formula

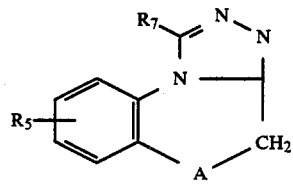

wherein A is selected from the group consisting of

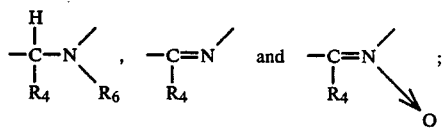

in which $R_5$ is selected from the group consisting of hydrogen, halogen, nitro, cyano, trifluoromethyl, lower alkyl, amino, hydroxy lower alkyl and lower alkanoyl; $R_4$ is selected from the group consisting of phenyl, monohalogen-substituted phenyl, dihalogen-substituted phenyl, pyridyl, thiophenyl, pyrimidinyl, oxazolyl, thiazolyl and 1-cyclohexenyl; $R_6$ is selected from the group consisting of hydrogen, lower alkyl, acyl, and lower alkoxycarbonyl; and $R_7$ is selected from the group consisting of hydrogen, lower alkyl, COO-lower alkyl, a radical of the formula

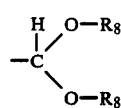

wherein $R_8$ is lower alkyl and a radical of the formula

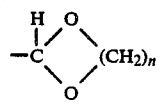

wherein n is an integer of 2 to 5,
which comprises reacting a compound of the formula

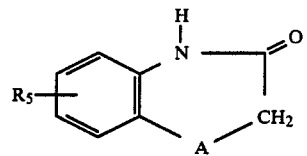

wherein A $R_5$, $R_4$ and $R_6$ are defined as above, with a strong base followed by a phosphorylating agent selected from the group consisting of dipiperazinophosphinic halides, dipiperidinophosphinic halides, dipyrrolidinophosphinic halides, dimorpholinophosphinic halides and bis-di-lower alkylaminophosphinic halides, and reacting the phosphorylated product with a compound of the formula H$_2$NNHCOR$_7$ wherein R$_7$ is defined as above.

2. A process for preparing a compound of the formula

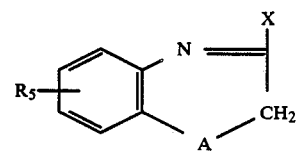

in which A is selected from the group consisting of

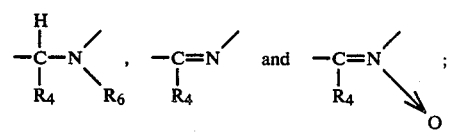

wherein $R_5$ is selected from the group consisting of hydrogen, halogen, nitro, cyano, trifluoromethyl, lower alkyl, amino, hydroxy lower alkyl and lower alkanoyl; $R_4$ is selected from the group consiting of phenyl, monohalogen-substituted phenyl, dihalogen-substituted phenyl, pyridyl, thiophenyl, pyrimidinyl, oxazolyl, thiazolyl and 1-cyclohexenyl; $R_6$ is selected from the group consisting of hydrogen, lower alkyl, acyl and lower alkoxycarbonyl; and X is a nucleophilic group selected from the group consisting of amino, monoalkylamino, dialkylamino, anilino, monomethylanilino, morpholino, piperidino, pyrrolidino, hydrazino, 2-hydrazinopyridino, 1,1-dimethylhydrazino, 1,2-dimethylhydrazino, methylhydrazino, 2-hydroxyethylamino, 2-aminoethylamino, methylhydrazinocarboxylate, acetylhydrazido, hydroxylamino, N-methylhydroxylamino and methoxylamino,
which process comprises reacting a compound of the formula

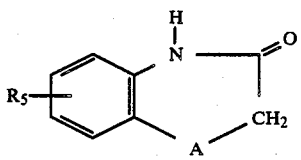

in which A and $R_5$ are as defined above, with a strong base, followed by a phosphorylating agent selected from the group consisting of dipiperazinophosphinic halides, dipiperidino phosphinic halides, dipyrrolidinophosphinic halides, dimorpholinophosphinic halides and bis-di-lower alkylamino phosphinic halides, to produce a compound of the formula

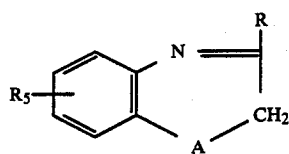

in which A and R₅ are as defined above and R is a leaving group of the formula

in which $R_1$ and $R_2$ independently are lower alkyl or together with the nitrogen atom form pyrrolidino, piperidino, 4-methylpiperidino, piperazino, or morpholino, and nucleophilically displacing the leaving group X in the presence of pyridine or triethylamine.

3. A process for preparing a compound of the formula

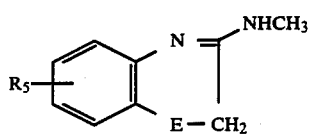

in which E is

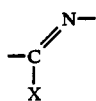

wherein R₅ is selected from the group consisting of hydrogen, halogen, nitro, cyano, trifluoromethyl, lower alkyl, amino, hydroxy lower alkyl and lower alkanoyl; and X is a nucleophilic group selected from the group consisting of amino, monoalkylamino, dialkylamino, anilino, monomethylanilino, morpholino, piperidino, pyrrolidino, hydrazino, 2-hydrazinopyridino, 1,1-dimethylhydrazino, 1,2-dimethylhydrazino, methylhydrazino, 2-hydroxyethylamino, 2-aminoethylamino, methylhydrazinocarboxylate, acetylhydrazido, hydroxylamino, N-methylhydroxylamino and methoxylamino, which process comprises reacting a compound of the formula

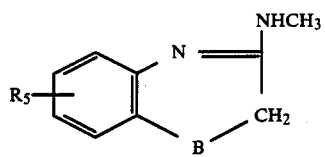

in which B is

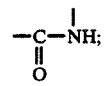

and R₅ is as defined above, with a strong base, followed by a phosphorylating agent selected from the group consisting of dipiperazinophosphinic halides, dipiperadinophosphinic halides, dipyrrolidinophosphinic halides, dimorpholinophosphinic halides and bis-di-lower alkylamino phosphinic halides, to produce a compound of the formula

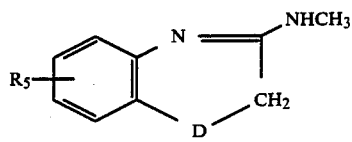

in which D is

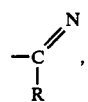

R₅ is as defined above and R is a leaving group of the formula

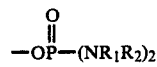

in which $R_1$ and $R_2$ independently are lower alkyl or together with the nitrogen atom form pyrrolidino, piperidino, 4-methylpiperidino, piperazino, or morpholino, and subsequently nucleophilically displacing the leaving group R with the nucleophilic group X in the presence of pyridine or triethylamine.

* * * * *